US010053672B2

(12) United States Patent
Vautherot et al.

(10) Patent No.: US 10,053,672 B2
(45) Date of Patent: Aug. 21, 2018

(54) METHOD FOR SELECTING A PERMISSIVE CELL LINE FOR REPLICATING AVIAN VIRUSES

(71) Applicant: INSTITUT NATIONAL DE LA RECHERCHE AGRONOMIQUE, Paris (FR)

(72) Inventors: Jean-François Vautherot, Monnaie (FR); Bertrand Pain, Nohanent (FR); Caroline Denesvre, Tours (FR); Laetitia Fragnet-Trapp, La Ferriere (FR)

(73) Assignee: INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 27 days.

(21) Appl. No.: 14/905,485

(22) PCT Filed: Jul. 24, 2014

(86) PCT No.: PCT/EP2014/065946
§ 371 (c)(1),
(2) Date: Jan. 15, 2016

(87) PCT Pub. No.: WO2015/011238
PCT Pub. Date: Jan. 29, 2015

(65) Prior Publication Data
US 2016/0152956 A1 Jun. 2, 2016

(30) Foreign Application Priority Data

Jul. 25, 2013 (FR) .................................. 13 57346

(51) Int. Cl.
| | |
|---|---|
| *C12N 7/00* | (2006.01) |
| *A61K 39/12* | (2006.01) |
| *C12N 5/077* | (2010.01) |
| *C12N 5/071* | (2010.01) |
| *A61K 39/255* | (2006.01) |
| *C12N 5/0735* | (2010.01) |
| *A61K 39/00* | (2006.01) |

(52) U.S. Cl.
CPC .............. *C12N 7/00* (2013.01); *A61K 39/12* (2013.01); *A61K 39/255* (2013.01); *C12N 5/0606* (2013.01); *C12N 5/0629* (2013.01); *C12N 5/0652* (2013.01); *A61K 2039/5156* (2013.01); *A61K 2039/5254* (2013.01); *C12N 2500/30* (2013.01); *C12N 2501/999* (2013.01); *C12N 2710/16334* (2013.01); *C12N 2710/16351* (2013.01); *C12N 2710/16352* (2013.01); *C12N 2720/10034* (2013.01); *C12N 2720/10051* (2013.01); *C12N 2720/10052* (2013.01)

(58) Field of Classification Search
None
See application file for complete search history.

(56) References Cited

U.S. PATENT DOCUMENTS 5,672,485 A * 9/1997 Foster .................. C12N 5/0652
435/235.1

FOREIGN PATENT DOCUMENTS

| EP | 0775743 A2 | 5/1997 |
| EP | 2572728 A1 | 3/2013 |
| WO | 98/06824 | 2/1998 |
| WO | 2007/110341 A1 | 10/2007 |
| WO | 2007/110343 A2 | 10/2007 |

OTHER PUBLICATIONS

Geerligs et al., Vaccine, 2008, 26(44):5595-5600.*
Blondeau, Marc, Courvoisier, Vautherot & Denesvre (2008). Functional homologies between avian and human alpha-herpesvirus VP22 proteins in cell-to-cell spreading as revealed by a new cis-complementation assay. J Virol 82, 9278-9282.
Chbab, Chabanne-Vautherot, Francineau, Osterrieder, Denesvre & Vautherot (2009). The Marek's disease virus (MDV) protein encoded by the UL17 ortholog is essential for virus growth. Vet Res 40, 28.
Churchill (1968). herpes-type virus isolated in cell culture from tumours of chickens with Marek's disease. I. Studies in cell culture. J Natl Cancer Inst 41, 939-950.
Coraux, Hilmi, Rouleau, Spadafora, Hinnrasky, Ortonne, Dani & Aberdam (2003). Reconstituted skin from murine embryonic stem cells. Curr Biol 13, 849-853.
Correia, Anisimov, Li & Brundin (2008). Growth Factors and Feeder Cells Promote Differentiation of Human Embryonic Stem Cells into Dopaminergic Neurons: A Novel Role for Fibroblast Growth Factor-20. Front Neurosci, 2, 26-34.
Denesvre, Blondeau, Lemesle, Le Vern, Vautherot, Roingeard & Vautherot (2007). Morphogenesis of a highly-replicative EGFPVP22 recombinant Marek's disease virus in cell culture. J Virol 81, 12348-12359.
Dorange, El Mehdaoui, Pichon, Coursaget & Vautherot (2000). Marek's disease virus (MDV) homologues of herpes simplex virus type 1 UL49 (VP22) and UL48 (VP16) genes: high-level expression and characterization of MDV-1 VP22 and VP16. J Gen Virol 81, 2219-2230.

(Continued)

*Primary Examiner* — Stacy Brown Chen
(74) *Attorney, Agent, or Firm* — Arrigo, Lee, Guttman & Mouta-Bellum LLP

(57) ABSTRACT

The present invention relates to a method for obtaining an untransformed avian cell line enabling in vitro avian virus replication. Said method includes the following steps: a) culturing avian embryonic stem cells in the presence of a stroma for at least 3 days; b) culturing for at least 2 days in a medium having a low serum concentration; c) culturing for at least 2 days in a medium having a low serum concentration containing 1 to 10 mM of hexamethyleme bisacetamide (HMBA); d) culturing for at least 10 days in a medium having a low serum concentration; and e) culturing or freezing an avian cell line enabling avian virus replication. The invention also relates to the resulting cell line and to the use thereof in vaccine preparations.

1 Claim, 7 Drawing Sheets

(56) References Cited

OTHER PUBLICATIONS

Esnault, Bonsergent, Larcher, Bed'hom, Vautherot, Delaleu, Guigand, Soubieux, Marc & Quéré (2011). A novel chicken lung epithelial cell line: Characterization and response to low pathogenicity avian influenza virus. Virus Res 159, 32-42.
Eyal-Giladi & Kovak (1976). From cleavage to primitive streak formation: a complementary normal table and a new look at the first stages of the development of the chick; I. General Morphology. Dev. Biol 49, 321-337.
Fuchs & Mettenleiter (1999). DNA sequence of the UL6 to UL20 genes of infectious laryngotracheitis virus and characterization of the UL10 gene product as a nonglycosylated and nonessential virion protein. J Gen Virol 80 ( Pt 8), 2173-2182.
Geerligs, Quanz, Suurland, Spijkers, Rodenberg, Davelaar, Jongsma, Kumar (2008). Efficacy and safety of cell associated vaccines against Marek's disease virus grown in a continuous cell line from chickens. Vaccine. 26, 5595-5600.
Jarosinski, Arndt, Kaufer & Osterrieder (2012). Fluorescently tagged pUL47 of Marek's disease virus reveals differential tissue expression of the tegument protein in vivo. J Virol 86, 2428-2436.
Jarosinski, Margulis, Kamil, Spatz, Nair & Osterrieder (2007). Horizontal transmission of Marek's disease virus requires US2, the UL13 protein kinase, and gC. J Virol 81, 10575-10587.
Jarosinski, Yunis, O'Connell, Markowski-Grimsrud & Schat (2002). Influence of genetic resistance of the chicken and virulence of Marek's disease virus (MDV) on nitric oxide responses after MDV infection. Avian Dis 46, 636-649.
Kawaguchi, Nomura, Hirayama & Kitagawa (1987). Establishment and characterization of a chicken hepatocellular carcinoma cell line, LMH. Cancer Res, 47, 4460-4463.
Kawasaki, Mizuseki, Nishikawa, Kaneko, Kuwana, Nakanishi, Nishikawa & Sasai (2000). Induction of midbrain dopaminergic neurons from ES cells by stromal cell-derived inducing activity. Neuron 28, 31-40.
Lavial, Acloque, Bertocchini, Macleod, Boast, Bachelard, Montillet, Thenot, Sang, Stern, Samarut & Pain (2007). The Oct4 homologue PouV and Nanog regulate pluripotency in chicken embryonic stem cells. Development, 134, 3549-3563.
Lee, Foster, Bottje, Jang, Chandra, Gentles & Kong. (2013). Establishment of an immortal chicken embryo liver-derived cell line. Poult Sci. 92,1604-1612.
Lejal, Da Costa, Huet & Delmas (2000). Role of Ser-652 and Lys-692 in the protease activity of infectious bursal disease virus VP4 and identification of its substrate cleavage sites. J Gen Virol 81, 983-992.
Marks & Rifkind (1989). Induced differentiation of erythroleukemia cells by hexamethylene bisacetamide: a model for cytodifferentiation of transformed cells. Environ Health Perspect. 80, 181-188.
Moscovici, Moscovici, Jimenez, Lai, Hayman & Vog (1977). Continuous tissue culture cell lines derived from chemically induced tumors of Japanese quail. Cell. 11, 95-103.
Mou, Pitel, Gourichon, Vignoles, Tzika, Tato, Yu, Burt, Bed'hom, Tixier-Boichard, Painter & Headon (2011). Cryptic patterning of avian skin confers a developmental facility for loss of neck feathering. PLoS Biol 9, e1001028.
Nakano , Kodama & Honjo (1994). Generation of lymphohematopoietic cells from embryonic stem cells in culture. Science 265, 1098-1101.
Ogura & Fujiwara.(1987). Establishment and characterization of a virus-free chick cell line. Acta Med Okayama. 41,141-143.
Pain, Clark, Shen, Nakazawa, Sakurai, Samarut & Etches (1996). Long-term in vitro culture and characterisation of avian embryonic stem cells with multiple morphogenetic potentialities. Development 122, 2339-2348.
Panacchia, Dellambra, Bondanza, Paterna, Maurelli, Paionni & Guerra. (2010). Nonirradiated human fibroblasts and irradiated 3T3-J2 murine fibroblasts as a feeder layer for keratinocyte growth and differentiation in vitro on a fibrin substrate. Cells Tissues Organs 191, 21-35.
Petherbridge, Brown, Baigent, Howes, Sacco, Osterrieder & Nair (2004). Oncogenicity of virulent Marek's disease virus cloned as bacterial artificial chromosomes. J Virol 78, 13376-13380.
Preston & McFarlane (1998). Cytodifferentiating agents affect the replication of herpes simplex virus type 1 in the absence of functional VP16. Virology 249, 418-426.
Richerioux, Blondeau, Wiedemann, Remy, Vautherot & Denesvre (2012). Rho-ROCK and Rac-PAK Signaling Pathways Have Opposing Effects on the Cell-to-Cell Spread of Marek's Disease Virus. PLoS One 7, e44072.
Schumacher, Tischer, Fuchs & Osterrieder (2000). Reconstitution of Marek's disease virus serotype 1 (MDV-1) from DNA cloned as a bacterial artificial chromosome and characterization of a glycoprotein B-negative MDV-1 mutant. J Virol 74, 11088-11098.
Schumacher, Tischer, Teifke, Wink & Osterrieder (2002). Generation of a permanent cell line that supports efficient growth of Marek's disease virus (MDV) by constitutive expression of MDV glycoprotein E. J Gen Virol 83, 1987-1992.
Solomon, Witter, Nazerian, Burmester (1968). Studies on the Etiology of Marek's Disease. I. Propagation of the Agent in Cell Culture. Exp Biol Med 127, 173-177.
Storlie, Jackson, Hutchinson & Grose (2006). Delayed biosynthesis of varicella-zoster virus glycoprotein C: upregulation by hexamethylene bisacetamide and retinoic acid treatment of infected cells. J Virol 80, 9544-9556.
Brown W S et al: "The avian EB66(R) cell line, application to vaccines, and therapeutic protein production", PDA Journal of Pharmaceutical Science and Technlogy>Bull Parenter Drug Assoc., Pareneral Drug Association, vol. 64, No. 5, Sep. 1, 2010 (Sep. 1, 2010), pp. 419-425.
Schaefer-Kljeient AL: "The EV-O-Derived Cell Line DF-1 Supports the Efficient Replication of Avian Leukosis-Sarcoma Viruses and Vectors", Virology Elsevier, Amsterdam, NL, vol. 248, No. 2, Sep. 1, 1998 (Sep. 1, 1998), pp. 305-311.
Kitagawa R et al: "Hexamethylene bisacetamide can convert nonpermissive humancells to a permissive state for expressing the major immediate-early genes of humancytomegalovirus by up-regulating NF-kappaBactivity", Virology, Elsevier, Amsterdam, NL, vol. 383, No. 2, Jan. 20, 2009 (Jan. 20, 2009), pp. 195-206.

\* cited by examiner

METHOD FOR SELECTING A PERMISSIVE CELL LINE FOR REPLICATING AVIAN VIRUSES

FIELD OF THE INVENTION

The present invention relates to a method for selecting a permissive cell line for replicating avian viruses, from avian embryonic stem cells.

INTRODUCTION

Poultry farms are affected or threatened by several viral diseases, the effects of which may be direct (virus-induced pathology) or indirect (immunodepression setting the stage for other viral, bacterial or parasitic infections).

Vaccination, widely practiced in the main annuity-providing avian species (chicken, turkeys, guinea fowl, quails, geese, ducks . . . ) however poses two problems:

The production costs of vaccines have to remain compatible with farming, only generating low profit margins for the farmer. Although the market is considerable in terms of vaccinated individuals (for example: 44 million laying hens in France in 2011), the vaccines can only be marketed at prices exceeding a few euro cents/dose.

Biosafety has to be ensured, especially during the use of attenuated living vaccines, potential vectors of contaminating pathogens. It should be recalled that breeding animals are vaccinated and that an accidental contamination at the top of the selection pyramid would have spectacular effects on the whole production chain.

From among the many pathologies of viral origin, Marek's Disease (MD) is an infectious lymphoproliferative disease affecting T cells in chickens. The clinical forms of MD mainly affect the hen (Gallus gallus), but other bird species from the order of Galliformes may also be infected and express symptoms (quails or turkeys). This disease gradually appeared as a major constraint for worldwide poultry production during the 60s. Marek's disease, considered as the second infectious disease for laying hens, has an overall impact estimated to be of 1,000 million $/year, these losses being related to the pathology and to the costs of vaccinations (FAO figure, 2002).

Marek's disease is due to a herpes virus of the sub-family of alpha herpes viridae of the *Mardivirus* genus, called Marek's disease virus (MDV) or Gallid herpes virus of type 2 (GaHV-2). The genus *Mardivirus* includes four other avian viruses: Gallid herpes virus of type 3 (GaHV-3), meleagrid herpesvirus (MeHV—HVT for herpes virus of turkeys) which more specifically affects turkeys, colombid herpes virus 1 (CoHV-1) which particularly affects Columbiformes, and anatid herpes virus 1 (AHV-1) which particularly affects anatidae (ducks, geese).

MDV rapidly propagates through poultry farms by direct contact of healthy animals with infected chicken, or by exposure to premises, litters, dust contaminated with debris of dander from infected animals. The entry of the virus takes place at the respiratory tracts, wherein lung lymphocytes B play an important role in the progression of the disease.

Extremely acute forms of the disease appeared in the 1990s, associated with the emergence of highly pathogenic viruses.

Since the 70s, vaccines have given the possibility of controlling Marek's disease in poultry farms. Only live vaccines are efficient and there exist two types of vaccines, those obtained by attenuation of GaHV-2 (homologous) or those derived from naturally apathogenic strains, MeHV-1 or GaHV-3 (heterologous). Vaccinal preparations derived from MeHV-1 are administered in ovo to embryos of 17-18 days old and the homologous vaccines are injected into chicks upon hatching. The infectiosity of the GaHV-2 virus is associated with living infected cells: there are no free virions detectable in the supernatants and in cell lyzates (Churchill, 1968). The propagation of the infection with GaHV-2 therefore requires in vitro co-cultivation of infected cells with naive cells or, in vivo, administration, by injection to the animals, of living infected cells. Present GaHV-2 vaccines therefore consist of cells infected in a cell culture and frozen.

STATE OF THE ART

The study of the relationships between the virus and the cells can only be carried out with so-called permissive cells and for the MDV, replication is restricted to avian cells. A cell is said to be permissive when it allows the virus to multiply and to produce new infectious virions. The genotype and the differentiation state of a cell are the two main factors determining the permissivity of a cell to infection by a virus.

The propagation of *Mardiviruses* in a cell culture is presently restricted to avian cells of primary or secondary explantation. Satisfactory replication levels are currently obtained on four different cell types: fibroblasts of chick embryos (CEF), fibroblasts of duck embryos (DEF) (Solomon et al., 1968), cells of chicken kidneys (CKC) (Churchill, 1968) or cells of chicken embryo skin (CESkC) (Dorange et al., 2000).

The small number of permissive avian cell lines allowing efficient replication of the avian viruses poses a problem both to scientists and to industrialists, producers of vaccines.

This problem is posed with great acuteness for *Mardiviruses*, for which no untransformed avian line is available to this day allowing efficient replication, i.e. producing, of all the *Mardiviruses*. The vaccines are therefore still exclusively produced on primary avian cells obtained by cultivating embryonic cells or by enzymatic dissociation of explanted organs of birds (Galliformes or Anseriformes). This assumes significant costs, production circuits and complex controls allowing certification of the absence of contaminating agents for each production cycle. Up to now, tests for isolating cell lines from explanted cells of organs or of embryos have proved to be not very fruitful.

At the present time, only one line derived from the DF-1 line (JB-J1) seems to be able to fulfill the essential criteria for industrial production of virus vaccines (Geerligs et al., 2008) without it being demonstrated that this line may be used as a substrate for replicating viruses not "adapted" to cell culture ("wild" viruses recovered on an infected animal). For these "wild" viruses, the only reported results relate to the use of a quail transformed cell line (QM7) over-expressing a gene of a viral glycoprotein, gE (Schumacher et al., 2002). These cells called SOgE support the growth of viral MDV-1 strains at a level comparable with the one observed on primary cultures of embryonic cells. Nevertheless, this last cell line derives from a transformed cell line i.e. capable of multiplying indefinitely, with in animals, a potential tumor-producing power related to the immortalization process; it is therefore dangerous to use such cells for preparing vaccinal preparations intended to be injected into chicken, since their proliferation is not under control. Further, SOgE cells are genetically modified organisms for which use is strictly regulated, and they will probably not be allowed for use in vaccinal preparations.

It should be noted that the DF1 cells (and therefore the JB-J1 which are derived therefrom) are obtained by spontaneous establishment of primary embryonic fibroblasts obtained from an embryo incubated for 10 days, as described in document WO98/006824. These cells are therefore derived from somatic cells already engaged in a differentiation route.

In the same way, CHCC-OU2 cells, described in patent application EP 775 746, are derived from embryo cells incubated for several days. These cells are established in a line by the immortalizing action of a chemical treatment of the primary cells with N-Methyl-N'-nitro N-nitrosoGuanidine (MNNG), as described in the publication of Ogura and Fujiwara (1987). The action of such a treatment on avian cells is known and results in the obtaining of an immortalized line, but having oncogenic properties. Thus, for example quail fibroblast cells QT6 which have also been obtained by chemical treatment have tumor-forming properties (Moscovici et al., 1977).

Further, the permissivity of CHCC-OU2 cells in replicating *Mardiviruses* is not established. As things stand, CHCC-OU2 cells do not form a system listed as permissive for *Mardiviruses*. Moreover, the derived line of CHCC-OU2 described in patent application EP 775 743 is a line chronically infected with an MDV virus, and not a permissive cell line for replicating *Mardiviruses*.

In the same way, Lee et al. (2013) describe cells obtained by immortalization of liver cells of an already incubated embryo, like obtaining the line LMH, itself derived from embryonic liver cells established subsequently to chemical treatment (Kawaguchi et al., 1987). These cells like in the case of QT6 cells are strongly tumorigenic. They are not described as fibroblasts, and are not or not very permissive to *Mardiviruses* (infectious titers=10 plate forming units (pfu) against 500,000 for ESCDL-1): therefore it is not established that the cells are capable of really replicating the virus, the residual 10 pfu's may be due to the persistence of DF-1 cells (a viral inoculum consisting of infected cells) during co-cultivation with CEL.im. cells.

Finally, the EB66 cells, described in patent application EP 2 572 728 are actually originate from embryos, like the cES cells at the origin of the ESCDL1 cells of the present invention. However, they retain the characteristics of ES cells, notably an expression of the markers cPOUV/OCT4 and NANOG. Further, these EB66 cells are not permissive to *Mardiviruses*.

DISCLOSURE OF THE INVENTION

The present invention relates to a method allowing obtaining a non-transformed cell line permissive to the replication of avian viruses, which may be used in vaccinal preparations.

The invention relates to a method for inducing differentiation of avian stem cells, resulting in the obtaining of a non-transformed line, derived from embryonic stem cells (ES), no longer expressing the characteristic markers of stem cells (cPOUV and NANOG), with stable phenotype over at least 60 passages after establishment and allowing replication of avian viruses.

The method comprises at least the following steps:
a) cultivating avian embryonic stem cells in the presence of a stroma for at least 3 days;
b) cultivating the cells from one of steps a), or c), or d) in a low serum concentration medium for at least 2 days;
c) cultivating cells from one of steps a), or b), or d) in a low serum concentration medium comprising between 1 and 10 mM of hexamethylene bisacetamide (HMBA), for at least 2 days;
d) cultivating the cells from one of steps a), or b), or c) in a low serum concentration medium for at least 10 days;
e) cultivating or freezing an avian cell line resulting from steps a), b), c) and d) allowing replication of avian viruses.

The invention also relates to the cell line as obtained with the method above, and to its use as a substrate for production in vitro of avian viruses.

The present invention also relates to the use of the cell line described above as a substrate for production in vitro of avian viruses or for titrating avian viruses.

Another object of the present invention moreover relates to a method for preparing in vitro a vaccinal preparation which comprises the cultivation of the line as described above and its infection with at least one avian virus, as well as to the vaccinal preparation, strictly speaking, which comprises a cell line as described above, infected with at least one avian virus.

DETAILED DESCRIPTION OF THE INVENTION

The present invention relates to a method for obtaining a non-transformed avian cell line allowing replication of avian viruses in vitro, comprising at least the following steps:
A) cultivating avian embryonic stem cells in the presence of a stroma for at least 3 days;
B) cultivating in a low serum concentration medium for at least 2 days;
C) cultivating in a low serum concentration medium comprising between 1 and 10 mM of hexamethylene bisacetamide (HMBA), for at least 2 days;
D) cultivating in a low serum concentration medium for at least 10 days;
E) cultivating or freezing an avian cell line allowing replication of avian viruses.

The method according to the invention has as "original product", or starting cells or initial cells, avian embryonic stem cells (cells ES), specifically expressing the markers cPOUV and NANOG as described in Lavial et al. 2007.

The differentiation of the avian ES cells by exposure to reduced serum concentrations is expressed by a morphological change (increase in cell size and increase of the cytoplasm/nucleus ratio) and the acquisition of low permissivity for replication of viruses "adapted" to the culture on cells.

The establishment of a permissive line from avian ES cells was conducted according to an induction logic based on the exposure to at least one complex extracellular matrix and to the cyto-differentiating action of HMBA.

The present invention gives the possibility of obtaining permissive cells to the replication of avian viruses which are established in a line, without resorting to the transformation by an oncogenic agent or an immortalization method by means of an external agent such as a chemical agent, unlike the cells of the prior art, in particular including the CHCC-OU2 cells. The cells of the invention are established by differentiation, notably by means of a cyto-differentiating chemical treatment (HMBA), and not by transformation or immortalization. The establishment of these permissive cells is therefore non-spontaneous, unlike certain cells of the prior art like the DF1 cells, since they derive from cells already established (ES cells) and not from a somatic primary cell.

Definitions

Generally, within the scope of the present invention, the expression "replication of avian viruses" should be understood as meaning an efficient and productive replication of viruses. Thus, by "permissive line of cells for replication of avian viruses", is meant a cell line or cells capable of accomplishing the whole of the steps of the viral cycle resulting in the production of a viral progeny consisting of infectious virions, and in particular of *Mardiviruses* and Birnaviruses (in the case of *Mardiviruses*, the infectious virions are associated with cells within an inoculum). As indicated above, a permissive cell allows the entry and the productive replication of the virus. The permissivity to the replication of avian viruses is variable from one virus to the other, which one skilled in the art will be able to appreciate from case to case, depending on the relevant viruses. One skilled in the art will thus be able to determine the sought multiplicative factor for each initial particle according to the type of tested virus.

The term of "cultivation in a suitable medium" is easily understandable for one skilled in the art, expert in cell cultivation. It refers to the fact of growing the cells in vitro and in a suitable nutritive medium, most often liquid, under conditions optimized for growth of cells, notably in terms of temperature and controlled $CO_2$ concentration. The "suitable medium" refers to a conventional culture medium, suitable for avian cells, comprising serum.

The term of "serum" refers to the blood liquid cleared of its cells and of the proteins for coagulation. It is the supernatant liquid obtained after centrifugation of blood, without any inhibitor of coagulation. This liquid contains a large number of nutrients (amino acids, vitamins . . . ), soluble proteins (antibodies, albumin, cytokines, growth factors, etc.) as well as various ions (sodium, chloride, etc.). In the present application, the term of "serum" refers both to fetal calf serum, conventionally used in cell cultivation, and chicken serum. A combination of both may be used, for associating the advantages of each serum. The serum is added to the culture medium according to a percentage of the total volume, i.e. about 100 ml of serum in one liter of total medium is expressed as a concentration of "10% of serum".

The expression <<low serum concentration or content>> refers to a percentage of serum of less than 5%, in particular 0.5%, 1%, 1.5%, 2%, 2.5%, 3%, or 4% of serum.

According to the invention, the term of "stroma" refers to a complex extracellular matrix derived from cells. For example, the stroma according to the invention may be prepared from primary cells of chicken skin according to the procedure described by Coraux (Coraux et al., 2003); it should be noted that in this publication, this stroma was used for differentiating mouse embryonic stem cells in epidermal tissue. The stroma may also be derived from cells permissive to avian viruses (stromal cell-derived inducing activity—SDIA—(Kawasaki et al., 2000)) or further from any type of cells non-permissive to viruses. Among the latter are comprised in a non-exhaustive list, mouse embryonic primary fibroblasts (MEFs), currently used as a nutritive coating after inactivation by action of mitomycin or irradiation, mouse fibroblasts established in lines such as STO cells (ATCC CRL 1503), allowing maintenance of ES cells, 3T3-J2 cells (Panacchia et al. 2010), marrow stroma cells like PA6 cells (also called MC3T3 G2) allowing neurectodermal differentiation (Correia et al., 2008), marrow stroma cells like OP9 cells (ATCC CRL2749) (Nakano et al., 1994) allowing induction of lymphopoietic differentiation, or of human or animal keratinocytes or any cell type having an advantage for one skilled in the art. Within the scope of the invention, one skilled in the art will be able to adapt the type of stroma to the type of differentiation.

The hexamethylene bisacetamide (HMBA—of chemical formula $CH_3CONH(CH_2)_6NHCOCH_3$) differentiation factor is known for its cyto-differentiating action towards murine cells of an erythroleukemic line in which differentiation is associated with a loss of capabilities to proliferate (Marks & Rifkind, 1989). Within the context of infections by herpes viruses, the induction by HMBA imparts to the cell either increased permissivity allowing replication of certain defective viruses (Preston & McFarlane, 1998), or increased expression of transcription factors PBX/HOX promoting viral replication (Storlie et al., 2006). HMBA is currently used, at doses from 1 to 10 mM, as a differentiation inducing agent for primary cells of chick embryo skin being used as a substrate for replication of *Mardiviruses* (Denesvre et al., 2007).

The term of "passage" refers to the cultivation of cells having attained a maximum occupation level of their support. The cells are detached from their support by rapid action of an enzyme or of a cocktail of protease enzymes (trypsin, pronase, dispase, collagenase) dissociating the cells from each other and promoting their detachment from the extracellular matrix ("trypsination" action) and are diluted in a culture medium before being sown on a new support for new cultivation of a few days. Conventionally, the cells detached from their support are counted before being sown at a certain ratio of cells/$cm^2$ in pretreated cultivation dishes for at least 20 minutes with 0.1% bovine gelatin solution in phosphate buffer (PBS), in order to provide the transferred cells with an extracellular matrix promoting their adhesion on the plastic support.

The different steps a), b), c) and d) are practiced for the required time. In particular, one skilled in the art will track the differentiation of the cells by viewing, by means of a microscope, their growth and their viability, and will be able to decide whether the step should continue beyond the indicated minimum time.

The cultivation step a) in the presence of a stroma will be carried out for at least 2 days, preferentially for at least 3 days, notably 3 days, more preferentially for 3 to 5 days.

The cultivation step b) in a low serum concentration medium will be carried out for at least 2 days, preferentially for 3 days.

The cultivation step c) in a medium comprising HMBA will be carried out for at least 2 days, preferentially for 3 days.

The cultivation step d) in a low serum concentration medium will be carried out for at least 10 days, preferentially for 15 days.

Preferably, after the various steps b), c) and d), the method further comprises steps for cultivating the cells in a suitable growth medium, in particular in a medium comprising more than 5% serum, and preferentially about 10% serum.

The last step e) corresponds to the obtaining of the permissive cell line to the replication of viruses, which may, depending on the cases, be used subsequently for replication of viruses or may be frozen according to the technique well known to one skilled in the art.

The method may be detailed as indicated below:
a) cultivating avian embryonic stem cells in the presence of a stroma for 4 days;
b) cultivating the cells in a low serum concentration medium for 3 days;
c) cultivating the cells in a medium containing 10% serum for 10 days;

d) cultivating the cells in a low serum concentration medium comprising between 1 and 10 mM of HMBA (hexamethylene bisacetamide), for 3 days;
e) cultivating the cells in a low serum concentration medium for 15 days;
f) cultivating or freezing an avian cell line allowing replication of avian viruses.

In a still more detailed way, the method may comprise the following steps:
a) cultivating avian embryonic stem cells in the presence of stroma for 4 days;
b) cultivating the cells in a low serum concentration medium for 3 days;
c) cultivating the cells in a medium containing 10% serum for 10 days and passage through trypsination;
d) cultivating the cells in a low serum concentration medium comprising between 1 and 10 mM of HMBA (hexamethylene bisacetamide), for 3 days;
e) passing of the cells through trypsination in a medium containing 10% serum for 3 days
f) cultivating the cells in a low serum concentration medium for 15 days;
g) passing of the cells through trypsination in a medium containing 10% serum for 12 days;
h) cultivating or freezing an avian cell line having a stable phenotype for at least 60 passages in a suitable culture medium and allowing replication of avian viruses.

All the steps a) to d), a) to f) and a) to h) of the method of the invention as described above may be carried out in any order, advantageously they are carried out in the order from a) to d), from a) to f) and from a) to h). For example, when the steps a) to d) are carried out in this order, the method of the invention comprises at least the following steps:
A) cultivating avian embryonic stem cells in the presence of a stroma for at least 3 days;
B) cultivating the cells from step A), in a low serum concentration medium for at least 2 days;
C) cultivating the cells from step B), in a low serum concentration medium comprising between 1 and 10 mM of hexamethylene bisacetamide (HMBA), for at least 2 days;
D) cultivating the cells from step C), in a low serum concentration medium for at least 10 days;
E) cultivating the cells from step D), or freezing an avian cell line allowing replication of avian viruses.

The resulting product of the method consists in permissive cells for replication of avian viruses, which may be maintained with the same phenotype for at least 60 passages in a suitable culture medium, and no longer expressing the markers cPOUV and NANOG characteristic of ES cells.

These cells were named "ESCDL-1" for "Embryonic Stem Cell Derived Line 1". The ESCDL-1 are adherent cells, of a fibroblast aspect, i.e. more spread out and less stretched than a primary fibroblast. They differ from the line of ES cells by their morphology, their growth characteristics, and the extinction of the expression of markers of ES cells.

This last characteristic also gives the possibility of distinguishing them from the cells of the prior art, such as EB 66 cells (see EP 2572 728) or the DF1, LMH, CEF and cES cells (BP25) (see Example 2 of the present application), in which the expression of markers of the cells ES is maintained. Thus, the ESCDL-1 cells of the invention do not express at least one of the following markers: cPOUV/OCT4, NANOG, SSEA1, EMA1, IXF1, KRT8 and KRT19. More preferentially, they do not express at least two, at least three, at least four, at least five or at least six of these markers. Still more preferentially, they do not express any of these markers.

Moreover, the ESCDL-1 cells of the invention strongly express the OLFM3 gene and the WISP1, THBS2 and EDN2 genes at levels comparable with those observed in primary fibroblasts.

The cells of the invention have a low telomerase activity as compared with that of the ES cells. The ESCDL1 cells are non-transformed cells and established in a line, which proliferate, but which are not tumorigenic unlike the lines established chemically or by the action of an exogenous immortalizing agent. The capability of proliferation of the ESCDL-1 cells (20% of the cells in phase S) is greater than that of primary cells of chicken embryo skin (CEPP) (3% of cells in phase S). Further, it is interesting to emphasize that the ESCDL-1 cells are sensitive to inductors of apoptosis and have a strong propensity of inducing autophagic processes in a medium depleted in growth factors or in the presence of an inducer of autophagy.

The method according to the invention gives the possibility of obtaining a permissive cell line for the replication of many avian viruses (notably herpes viruses, Pox viruses, Corona viruses, Birnaviruses, Reo and Rotaviruses) and in particular for *Mardiviruses* and Birnavirus, an agent of infectious bursitis (IBDV).

According to a preferred aspect of the invention, the starting or initial avian embryonic stem cells are chicken cells. Preferentially, the ES cells stem from a chicken with the heterozygote Cou-nu genotype (Na/na).

More preferentially, the initial avian embryonic stem cells are blastodermal isolated cells of stages X to XIV (according to Eyal Giladi and Kovak, 1976). Unlike certain cells of the prior art, the cell line according to the invention originates from embryos, not incubated since it derives from embryonic stem cells, themselves obtained from the cultivation of these non-incubated blastodermal cells.

These initial avian embryonic stem cells express many marker genes such as those shown in patent application WO 2007/110343, and in particular the marker genes cPOUV and NANOG.

According to a preferred aspect of the invention, the avian cell line obtained has a stable phenotype for at least 60 successive passages, preferentially at least 70 passages, more preferentially at least 80 passages, from its establishment.

Preferentially, the phenotype characteristics of the avian cells according to the invention are more particularly the following:
Morphology of the fibroblast/mesenchymatous type;
Expression of CD44, beta1 integrin, and collagen 1;
No expression of markers of ES cells, notably including cPOUV and NANOG, KRT19 and KRT8, but strong expression of the OLFM3 gene and sustained expression of the WISP1, THBS2 and EDN2 genes at levels comparable with those observed in primary fibroblasts; and
Permissivity to the replication of *Mardiviruses* and avian Birnaviruses.

By mesenchymatous fibroblast cell, is meant a cell having a morphology similar to that of the not very differentiated cells of connective tissues with notably long extensions and an ovoidal nucleus at the centre of the cell.

According to another aspect of the invention, the avian cell line obtained may be genetically modified for expressing proteins of interest. The proteins of interest may be "reporter" proteins (fluorescent proteins; enzymes such as the different forms of luciferases or phosphatases . . . ), enzymes for modifying the genome (recombinases), autologous or heterologous viral proteins which may intervene as a complementation for viruses for which certain genes have been deleted, or further cell proteins for which overxpression may have an impact on viral replication.

As shown in the examples, even genetically modified as described above, the avian cell line according to the invention retains its permissivity to avian viruses.

The present invention also relates to a cell line which may be obtained by the method described above, i.e. a non-transformed cell line allowing replication of avian viruses in vitro, in particular both *Mardiviruses* and Birnaviruses.

In particular, this cell line expresses the following markers: CD44$^+$, beta1 integrin, and collagen 1. On the other hand it no longer expresses the antigens recognized by the antibodies IXF1, MC-480 (SSEA1) and EMA-1 while the latter are expressed by initial embryonic stem cells. They no longer express the genes cPOUV/OCT4, NANOG, KRT19 and KRT8 but strongly express the gene OLFM3 and the genes WISP1, THBS2 and EDN2 at levels comparable with those observed in primary fibroblasts (taken equal to 1 in the figure). The level of these genes in the fibroblast cells DF1 is 10 to 100 times lower (FIG. 5). In the same way, liver cells LMH do absolutely not have the same profile for expression of these markers. The present invention also relates to a use of the cell line described above as a substrate for the production in vitro of avian viruses.

The present invention also relates to a use of the cell line as described above for titration of avian viruses, and thus determining the importance of the viral infection.

Finally, the present invention also relates to a method for preparation in vitro of a vaccinal preparation, comprising the cultivation of the line as described above and its infection with at least one avian virus. In other words, the invention relates to a method for preparing in vitro a vaccinal preparation, comprising at least the following steps:
A) cultivating avian embryonic stem cells in the presence of a stroma for at least 3 days;
B) cultivating in a low serum concentration medium for at least 2 days;
C) cultivating in a low serum concentration medium comprising between 1 and 10 mM of hexamethylene bisacetamide (HMBA), for at least 2 days;
D) cultivating in a low serum concentration medium for at least 10 days;
E) cultivating or freezing an avian cell line allowing replication of avian viruses;
F) infecting the cell line obtained with at least one avian virus.

The present application also relates to a vaccinal preparation comprising a cell line as described above, infected with at least one avian virus.

Within the scope of the different uses specified above, the avian viruses are in particular selected from among *Mardiviruses* and Birnaviruses.

EXAMPLES

Materials and Methods

Figure 1:
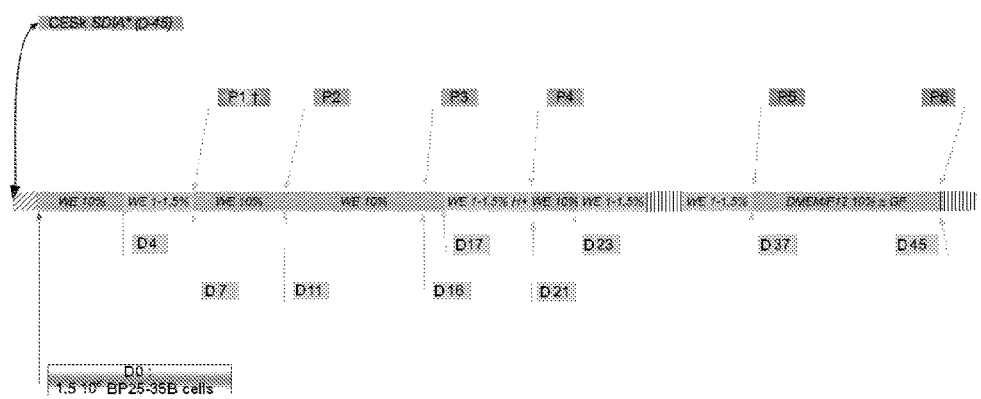
FIG. 1. Procedure for establishing the ESCDL-1 line: The initial induction period for the BP25-36b cells is illustrated between days 0 and 45 by the central bar, showing the alternation of the media used for cultivating the cells. The count of passages is indicated above, passages 1 to 6 (P1 to P6). P1† in fact corresponds to short trypsination intended to remove the dead cells followed by incubation in a 10% FCS medium. The count of the days relatively to the initiation of the culture appears below the central bar (D0 to D45). The indicated media are William's E medium (WE) or DMEM/F12. The 1-1.5% concentrations relate to FCS concentrations (1%) and chicken serum concentrations (1.5%). The acronym GF corresponds to "growth factors", as used in the growth medium of the BP25 cells and described in the equipment and method.

1. Growth factors, chemical products and antibodies

The growth factors (PeproTech—France) for growing avian embryonic stem cells were used in the following concentrations:

IGF-1 (PeproTech-100-11) at 5 ng/ml
IL6 (PeproTech-200-06) at 2 ng/ml
sIL6-Ra (PeproTech-200-06R) at 2 ng/ml
SCF (PeproTech-300-07) at 1 ng/ml
HMBA [N,N'-Hexamethylene bis(acetamide)—ref. 224235], retinoic acid (ref. R2625), DMSO (Dimethyl sulfoxide—ref. D2650), valproate (valproic acid, sodium salt—ref. P4543) were purchased from Sigma—Aldrich (Sigma Aldrich—France) and used at the concentrations indicated in the text.

2. Cells
a. BP25 stem cells: the cells were sustained under the described conditions (Pain et al., 1996), on a feeder layer of irradiated STO cells, in a DMEM/F12 medium (1:1) (Gibco—Invitrogen—France) added with 10% of fetal calf serum (FCS) (PAN—D. Dutscher—France), sodium pyruvate (1 mM—Lonza—France), glutamine (2 mM—Lonza—France) and non-essential amino acids (NEAA 100×—Lonza—France) and containing the growth factors at the concentrations indicated in the previous paragraph (ES medium).

b. ESCDL-1 cells: The ESCDL-1 cells were obtained by differentiation of the BP25 cells (cf. infra). The cells are cultivated at 37° C., in an atmosphere containing 5% $CO_2$, in a DMEM/F12 medium (1:1) (Invitrogen—France) added with 10% of FCS (PAN—D. Dutscher—France), sodium pyruvate (1 mM—Lonza—France), glutamine (2 mM—Lonza—France) and non-essential amino acids (NEAA 100×—Lonza—France). The cells are trypsinated twice a week (trypsin 10×—T4549—Sigma Aldrich—France) and divided according to a ratio of 1 to 3.

c. Chicken embryo skin primary cells (CESkC): the primary cells were obtained according to the described procedure (Dorange et al., 2000).

d. 3867K and NWB cells: the lines transformed with the RB-1B-UL47EGFP virus (Jarosinski et al., 2012), obtained in the laboratory of V. Nair, were cultivated in an RPMI 1640 medium (Lonza—France) containing 10% FCS, 10% of trypose phosphate broth (TPB) (ref. T8782 —Sigma Aldrich—France) and 4.5 g/l of glucose. The 2 transformed lymphocyte lines 3767K and NWB came from kidney tumors sampled on chicken infected with the RB-1B-UL47EGFP virus (the lines were given to us by Lorraine Smith—The Pirbright Institute—Compton, Berkshire, UK).

3. Viruses a. GaHV-2 (MDV)
  i. Bac20 and derived viruses: The Bac20 viruses (Schumacher et al., 2000), Bac20eGFPVP22 (Denesvre et al., 2007) and the Bac2OUL17-mRFP (Chbab et al., 2009) were obtained by transfection of bacmids containing the parent (Bac20) or mutated viral genome.
  ii. RB-1B and derived viruses: the virus RB-1B was obtained under conditions of bacmid transfections similar to those described for Bac20, from the bacmid described by L. Petherbridge (Petherbridge et al., 2004). The virus RB-1B-UL17mRFP was constructed according to the same logic as Bac2OUL17-mRFP within the context of the RB-1B bacmid described by Jarosinski (Jarosinski et al., 2007). The virus RB-1B-UL47EGFP (Jarosinski et al., 2012) was obtaining by putting tested cells into contact with the 3867K or NWB cells.

b. MeHV1: the vaccinal strain FC-126 was passed into a culture from a freeze-dried vaccinal preparation (Lyomarex®—Mérial—France). All the inocula of *Mardiviruses* (GaHV-2 and MeHV1) consist of infected, freeze-dried cells kept in liquid nitrogen.

c. GaHV-1 (ILTV): the virus used corresponds to the vaccinal strain Nobilis® (Intervet—France). The virus was produced on LMH cells from the freeze-dried vaccinal preparation. The viral inocula were kept at −80° C. after centrifugation at 200×g of the supernatants from infected cells (Fuchs & Mettenleiter, 1999).

d. IBDV: the Birnavirus of infectious chicken bursitis, vaccinal strain CT, was given to us as an infected culture supernatant by B. Delmas (Lejal et al., 2000).

4. Differentiation of the stem cells a. Exposure to cyto-differentiating agents: the BP25 cells in an exponential growth phase were trypsinated, counted and sown at $1·10^5$ cells/$cm^2$ in culture dishes pretreated with a solution of bovine gelatin (bovine gelatin with 0.1% PBS—ref. G9391 Sigma—France). After 24 hours at 37° C. in William's E medium containing 10% of fetal calf serum, the cells were incubated for 24 to 48 hours in the same medium containing 3% of chicken serum (SP) (Gibco—InvitroGen—France) and 2% of fetal calf serum (FCS). The confluent layers were exposed for 24 hours to different cytodifferentiating molecules in a William's E medium containing 1% of FCS and 1.5% of SP (WE 1-1.5%) and then infected (cf. infra).

b. ESCDL-1: the cells BP25 at passage 36 were sown at $1.5·10^6$ cells in a dish of 75 $cm^2$ containing an extracellular matrix prepared from primary cells (CESkC) according to a suitable procedure from the publication of C. Coraux (Coraux et al., 2003). The cells were first cultivated in a WE medium with 10% SF for 4 days (FIG. 1) and then incubated in a WE medium with 1% FCS-1.5% SP for 3 days with a change of medium. After trypsination, the cells were re-cultivated in dish of 75 $cm^2$, in WE containing 10% of FCS for 10 days, trypsinated and exposed to induction by HMBA (5 mM) in WE 1% FCS-1.5% SP for 72 hours (ESCDL-1 passage 3). The cells were trypsinated, sown on a gelatin culture support and cultivated in WE with 10% FCS during 1 passage (P4). The cells were then incubated for 15 days in WE with 1% FCS-1.5% SP trypsinated and cultivated in a DMEM-F12 medium containing 10% of SF (P5 to P7). From passage 7, the cells were trypsinated twice a week, divided according to a ratio of 1 for 3, and cultivated until the passage 18 in the same medium. The cells were kept in liquid nitrogen starting from this passage (P18)

5. Transfection: The ESCDL-1 cells were transfected by using the Amaxa™ technology (Amaxa Nucleofector—Lonza—France), with the Basic Fibroblast kit (ref. VPI-1002) and plasmid and bacmid DNA amounts varying from 4 to 8 µg for $4·10^6$ cells. After transfection, the cells were distributed in 3 wells of a 6-well cultivation plate, with gelatin beforehand, and cultivated for 16 hours in a DMEM/F12 medium containing 10% of FCS. The cells were placed in a medium matching the experiment (cf. infra). For selecting stable lines expressing transgenes under a pCMV promoter in pCDNA3, the cells were placed in a selection medium, DMEM/F12 with 10% FCS containing 0.5 mg/ml of G418 (Ref.—Sigma Aldrich) following the first trypsination 24 to 48 hours after transfection. In the absence of a selection gene on the plasmid coding for the transgene, the latter was co-transfected with a plasmid providing a gene for resistance to hygromycin (pTK-HYG2). In this case, the cells were placed in a selective medium (DMEM/F12 10% FCS with 80 µg/ml of hygromycin) as soon as 24 hours after the transfection.

6. Viral infections a. Preparation of the inocula
  i. Transfection of bacmids: in ESCDL-1 cells, the bacmids containing viral genomes were transfected by means of the Amaxa technology. In the induced CESC BP25, the bacmids were tranfected by means of the reagent FuGENE (Roche) by observing the instructions of the manufacturer. After transfection, the ESCDL-1 cells were incubated in a DMEM/F12 10% FCS medium for 16 hours and then in a DMEM/F12 medium containing 1% of FCS, 1.5% of SP and 0.3 mM of ascorbic acid. The BP25 cells induced were replaced in WE 1-1.5% with the inducers at the described concentrations.
  ii. Use of sorted infected cells: the preparation of the sorted infected cells has been described (Denesvre et al., 2007). After incubation for 1 h 30 to 2 hours at 37° C., the inocula (sorted cells) are removed and the ESCDL-1 cells are replaced in a DMEM/F12 medium containing 1% of FCS, 1.5% of SP and 0.3 mM of ascorbic acid. The induced BP25 cells are replaced in WE 1-1.5% with the inducers at the described concentrations.

iii. Use of transformed lymphocytes: the NWB or 3867K cells were centrifuged, placed in a low fetal serum concentration medium (DMEM/F12) and sown on a confluent layer of ESCDL-1 cells. After incubation for 1 h 30 at 37° C., the inoculum was removed and the medium replaced with DMEM/F12 medium containing 1% of FCS, 1.5% of SP and 0.3 mM of ascorbic acid.

iv. Freezing the inocula: in every case, the inocula are prepared from layers of infected cells having maximum cytopathogenic effect. After trypsination and centrifugation (200×g for 10 minutes), the cell pellets were taken up in a freezing mixture consisting of 95% of FCS and 5% of DMSO and the cells were distributed in cryotubes according to a ratio of 3 tubes/75 cm² dish. After 24 hours in an isothermal dish at −80° C., the tubes were transferred into liquid nitrogen.

b. Titrations: The titrations were carried out on cell layers 48 h after sowing, on primary cells (CESkC) or on ESCDL-1 cells. The method described earlier (Blondeau et al., 2008) was adapted to the context of ESCDL-1 cells in that the DMEM/F12 medium was substituted for WE and that, after inoculation, the cell layers were placed in a semi-solid medium consisting of DMEM/F12 or WE containing 1% of methylcellulose (methylcellulose ref. 25 449.182—VWR-Prolabo), 1% of FCS, 1.5% of SP and 3 mM of ascorbic acid (ESCDL-1). After 3 days (Bac20 and mutants) or 4 days (RB-1B and mutants), the cell layers were fixed by incubation in the presence of a paraformaldehyde solution (ref. P6148—Sigma Aldrich—France) with 4% of PBS buffer for 20 minutes at room temperature. The fixation solution was then removed, and the layers were rinsed with PBS. For detecting viral antigens, the cells were permeabilized and the immunofluorescence reaction was conducted according to a described procedure (Dorange et al., 2000). The measurement of the sizes of plates in different cell contexts was conducted according to the procedure described by N. Richerioux (Richerioux et al., 2012), on an average number of 80 individualized plates.

c. Viral load: The number of copies of viral genome per cell was estimated by using a quantitative PCR reaction (qPCR) of the Taqman type, according to the procedure described by K. Jarosinski (Jarosinski et al., 2002). Briefly, the cell gene iNOS and the viral gene ICP4 are quantified in samples by means of a pair of primers and a specific probe for each gene. (Table 2). In order to quantify the measurements in copy numbers, a dilution range with a known number of DNA copies of each target gene was used. The iNOS standard is a pBS-iNOS plasmid (donation from K. Jarosinski) adjusted to a concentration of 5 ng/µL, stored at −20° C. The ICP4 standard is a BAC-20 bacmid adjusted to 50 ng/µL, stored at 4° C. The dilution ranges of the standards are produced from $10^{-3}$ to $10^{-7}$ in water. The qPCRs were carried out in 96—well plates with the Absolute-Blue qPCR Mix& ROX kit (ABgene), the pairs of primers as well as the probes (Eurogentec). The reactions were conducted in a final volume of 20 µL (10 µL of Mix Fast Blue 2×+0.10 µL of each primer at 100 µM+0.5 µL of probe at 10 µM+9.5 µL of DNA).

7. Detection of cell and viral antigens.

a. Immunofluorescence: The cells were cultivated on a glass slide with a diameter of 14 mm and the thickness of 0.17 mm (Marienfeld—VWR—France), in a 24—well plate (ref. 353935 BD Falcon—France) after the slides were incubated in 0.1% gelatin in PBS for 30 minutes. The cells were fixed with 4% paraformaldehyde. The conditions for completing the immunofluorescence reaction on fixed and permeabilized cells have been described (Chbab et al., 2009). On non-permeabilized cells, the whole of the incubations was carried out in a PBS buffer containing 2% of bovine serum albumin (BSA) (fraction V—PAA—France). The primary antibodies used are described in table 1. The secondary antibodies used, anti IgG of mice, anti IgG of rabbit or anti IgG of chicken, are coupled with Alexa 488 or 594 (Molecular Probes—Invitrogen—France). Polymerized actin (F-actin) was marked with phalloidin coupled with Alexa 594 (Ref. A12381—Molecular Probes—Invitrogen—France). The photographs were taken with a Zeiss Axiovert 200M® microscope equipped with a Colibri II®, an Apotome® Zeiss device of an AxioCam MRm Zeiss® camera and controlled by Axiovision software (Carl Zeiss SA—France).

b. Immunoimprint (WB). The conditions under which viral antigens were detected from ESCDL-1 cell extracts were the same as those described for the primary cells (Chbab et al., 2009).

8. Transmission electron microscopy: the ESCDL-1 cells at passage 25 were infected with a Bac20 virus at passage 3 after transfection on these same cells. The cells were cultivated on a 6—well plate UpCell (Nunc UpCell surface Ref. 174901—Thermo Scientific—France) under the described infected conditions (cf. supra), (or "mock" infected for control cells) and the layers were recovered according to the procedure described by the supplier so as to be then fixed in Trump's fixative. The infected or non-infected cells were prepared for examination in electron microscopy according to a procedure described previously (Denesvre et al., 2007).

Results

Example 1

Isolation of the ESCDL-1 Line

The establishment of a permissive line from BP25 cells was conducted according to an induction logic based on successive exposure to complex extracellular matrices derived from permissive cells (Stromal cell-derived inducing activity—SDIA—(Kawasaki et al., 2000)) and to the cytodifferentiating action of HMBA. The preparation of the extracellular matrices from chicken skin primary cells was carried out according to the procedure described by Coraux (Coraux et al., 2003). The culture supports obtained were stored for 45 days at 4° C. and absence of cell growth was checked at the end of the storage. On day 0 of the induction, the stem cells were sown on a Petri dish containing the extracellular matrix, in an amount of 26,500 cells/cm², in a WE medium containing 10% of FCS (FIG. 1). After a cycle of exposure to reduced serum concentrations and 2 trypsinations, the cells at the passage 3 were exposed for 3 days to the action of HMBA (5 mM), in a WE medium containing 1% of FCS and 1.5% of SP. The continuation of the establishment procedure (FIG. 1) took place over a period of 25 days, included 3 trypsinations resulting in the passage 6 after establishment of the culture. The cells were then transferred into a DMEM/F12 medium containing 10% of FCS, a medium in which they were then cultivated. The trypsination rate passed from 1 a week (passages 6 and 7) to 2 a week for passages 8 and the following passages, with an average sowing of 45,000 cells per cm². In parallel to the establishment of the line, the permissivity for viral replication was tested on a one-off basis at passage 13, revealing multiplication of the Bac20 virus on ESCDL-1 cells. The line was considered as established from passage 23 and inventories of frozen cells were made up starting from passage 18.

Example 2

Characterization of the ESCDL-1 Line

Figure 2:
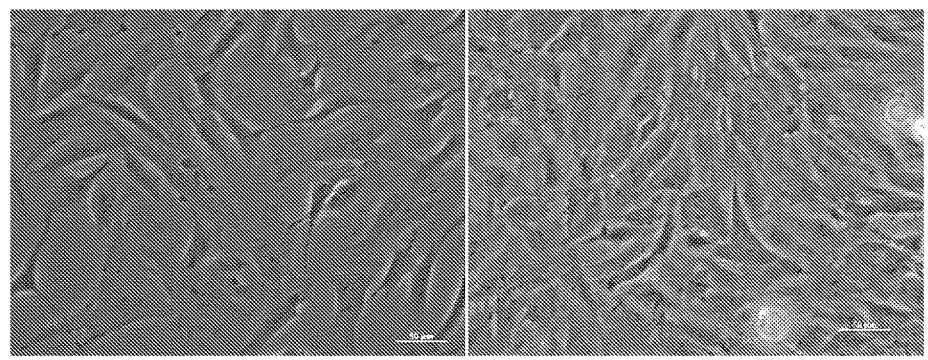
FIG. 2. ESCDL-1 cells: cells at passage 52, in a culture with low (A) or medium (B) density for 24 hours after division. The scale bar represents 50 µm (phase contrast microscopy).
Figure 3:
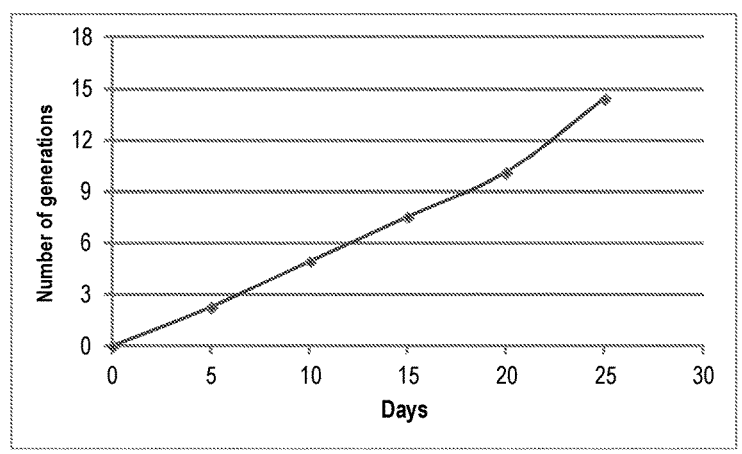
FIG. 3. The growth curve for ESCDL-1 cells between the passages 25 and 30.

The ESCDL-1 cells have a rather fibroblast morphology (FIG. 2), their doubling period is of about 40 hours and they seem to show gradual loss of their proliferation potential from the $100^{th}$ passage. Their growth curve is shown in FIG. 3.

The lineage between BP25-36b and ESCDL-1 was checked so as to establish that the cells did not derive from the persistence of living cells from among the cells having been used for establishing the extracellular matrix. As the BP25 cells were obtained from naked neck chicken embryos (Pain et al., 1996), we used a PCR differentiating LD1 animals from naked-neck animals (Mou et al., 2011) on genomic DNAs extracted from stem cells (BP25), from ESCDL-1 (P38) cells and from skin embryo primary cells (LD1 hens). The analysis of the fragments obtained showed that the BP25 like the ESCDL-1 derive from an embryo of the naked-neck genotype (heterozygote—Na/na) while the primary cells stemmed from a "wt" genotype (homozygote na/na).

Figure 4:
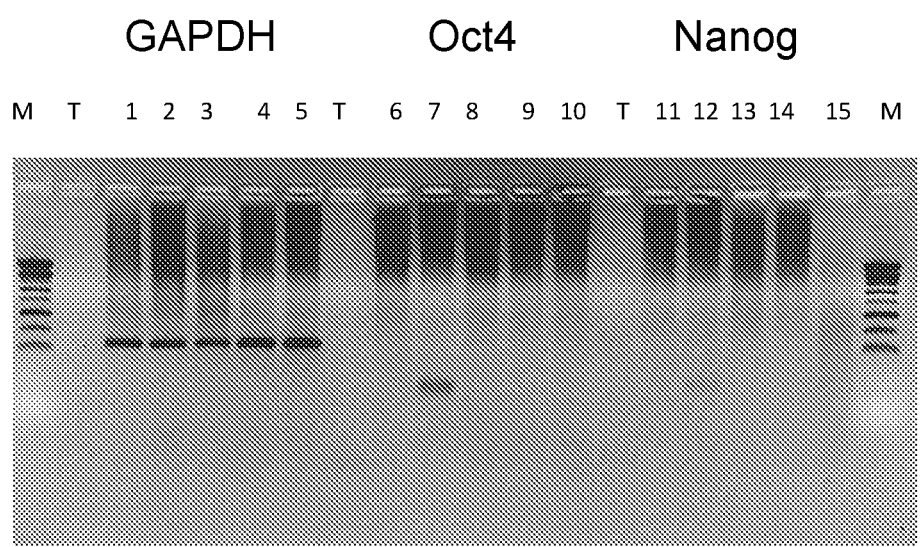
FIG. 4. Gene expression of the markers of stem cells in RT-PCR: Oct4 (cPOUV) and NANOG.

FIG. 4 illustrates the detection of messenger RNAs of Oct4 and NANOG markers in BP25 and ESCDL-1 cells, by the RT PCR technique. Only the stem cells BP25 express the mRNA of the markers OCT4 (7) and NANOG (12). These mRNAs are undetectable in ESCDL-1 cells (wells 10 and 15). The detection of the mRNAs of GAPDH in all the RNA preparations (1 to 5) is a witness to the uniform quality of the skin mRNA preparations (1-6-11), stem cells BP25 (2-7-12), liver (3-8-13) cells, kidney (4-9-14) cells and ESCDL-1 cells (5-10-15). These results were confirmed with qRT PCR. In immunofluorescence, it proved to be impossible to view the expression of other markers of stem cells in the ESCDL-1 cells (Table 1).

TABLE 1

Comparison of the expression of the pluripotential markers on BP25 cells and ESCDL-1 cells (the MDCK cells were used as a control). The membrane antigens SSEA-1 (characteristic of ES cells) and EMA-1 membrane antigens (considered as a good marker of PGC cells) were detected on BP25 cells by indirect immunofluorescence while the ESCDL-1 cells did not exhibit any marking.

| | | Cells (non-permeabilized) | | |
| --- | --- | --- | --- | --- |
| Antibody | Specificity | ESCDL-1 P39 | BP25 | MDCK P22 |
| IXF1 | Epithelial StemCell Marker | − | + | − |
| MC480 | SSEA-1 | − | + | − |
| EMA-1 | PGC marker | − | + | − |
| TROMA-1 | CytoK-EndoA | − | − | + †? |

Finally the telomerase activity was measured in ESCDL-1 cells as compared with LMH cells (positive control) and other cell lines (DF1 and CLEC) and primary cells (CES kC); low activity may be detected, comparable with that observed for DF1 and CLEC cells (Esnault et al., 2011), but considerably lower than the one observed in LMH cells.

Figure 5A:
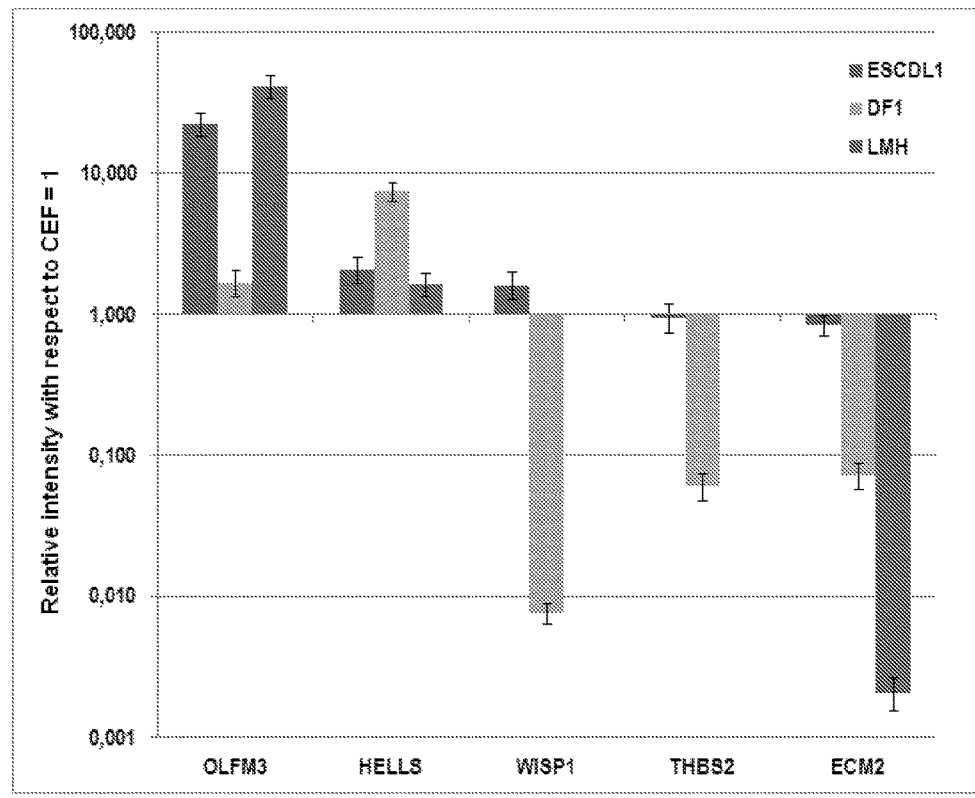
FIG. 5. a) Analysis of the expression of differentially expressed genes between the ESCDL1, DF1 and LMH cells. The expression level of the genes is measured by real time PCR, the gene RSP17 being taken as a reference as described earlier (Lavial et al., 2007). The relative expression level is taken equal to 1 in the cell type of the CEFs, primary embryonic fibroblasts of chicken. b) Analysis of the expression of genes more specifically expressed in embryonic stem cells (cES). The expression level in these cells is taken to be equal to 1. The levels in the ESCDL1, DF1 and LMH cells are much lower (between 1,000 to 10,000 times less expressed) or even undetectable in certain cases (NANOG for ex).
Figure 5B:
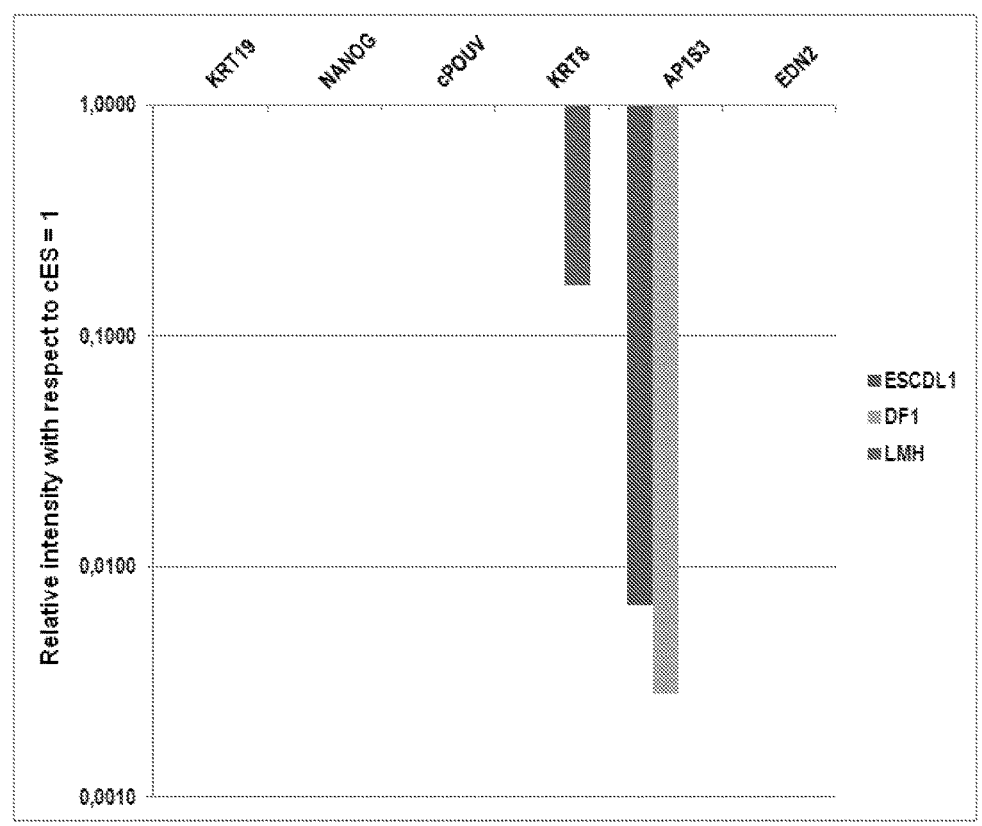
Figure 6:
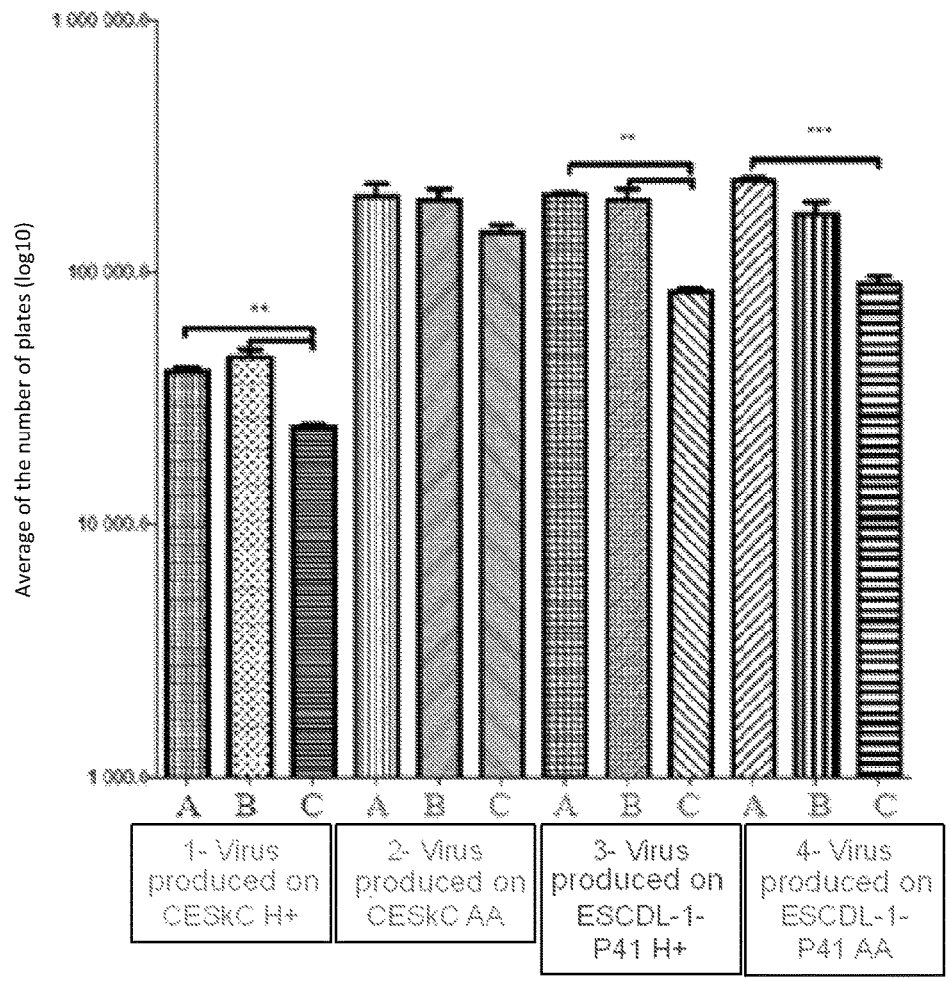
FIG. 6. Replication of the *Mardiviruses*: Comparison of the viral production (B2OUL17mRFP) on the primary cells (1 & 2) with that obtained on the ESCDL-1 P41 (3 & 4). The titrations were carried out on primary cells (A), ESCDL-1 at passages 43 (B) and 98 (C). H+: HMBA 5 mM; AA: Ascorbic Acid 0.3 mM.

A comparative analysis by RT-PCR (Lavial et al., 2007) of the expression of pluripotential genes (5a) and of marker genes of fibroblasts (5b) among DF1, LMH, CEF, cES (BP25) and ESCDL-1 cells obtained according to the invention was carried out, as to the presence of certain markers. The primers used for this analysis are listed in Table 2 below. The results of this analysis are grouped in FIGS. 5a and 5b.

TABLE 2

| Name of the gene | Gene ID | Sense | AntiSense |
| --- | --- | --- | --- |
| AP1S3 | 424807 | TGCGGTGAAAGCCATGGAAGAC (SEQ ID NO: 1) | GCAGGTGTGTACAGCAGTTCTCTTTCC (SEQ ID NO: 2) |
| cPOUV/OCT4 | 427781 | TGCAATGCAGAGCAAGTGCTGG (SEQ ID NO: 3) | ACTGGGCTTCACACATTTGCGG (SEQ ID NO: 4) |
| ECM2 | 415953 | GTCAGAAATTTGCTTTAACCACACAAG (SEQ ID NO: 5) | TTTATCCAAGCCAAAGGTGCTATTC (SEQ ID NO: 6) |
| EDN2 | 419559 | CTGGAGCCCAAGGCAGACGC (SEQ ID NO: 7) | GGCCAGTGATGCGGGCACTT (SEQ ID NO: 8) |
| HELLS | 423750 | AAGCTCTGCTGGCAACCTGTGTC (SEQ ID NO: 9) | AGGAACTGCTTGGCACTGTGTCG (SEQ ID NO: 10) |
| KRT19 | 395861 | GGCTTCGGTGGTGGCTATGG (SEQ ID NO: 11) | AGGACGCGAGGCGGTCATTC (SEQ ID NO: 12) |

TABLE 2-continued

| Name of the gene | Gene ID | Sense | AntiSense |
|---|---|---|---|
| KRT8 | 426896 | CCGGCAGCTGCGTGAGTACC (SEQ ID NO: 13) | CGTGGTCCGGGTGTGGATGC (SEQ ID NO: 14) |
| NANOG | 100272166 | TGCACACCAGGCTTACAGCAGTG (SEQ ID NO: 15) | TGCTGGGTGTTGCAGCTTGTTC (SEQ ID NO: 16) |
| OLFM3 | 424461 | TGGGCAGGAACCAACCACGTT (SEQ ID NO: 17) | GTGCAAGCACCCGCCCAGTA (SEQ ID NO: 18) |
| RSP17 | 374053 | ACACCCGTCTGGGCAACGAC (SEQ ID NO: 19) | CCCGCTGGATGCGCTTCATC (SEQ ID NO: 20) |
| THBS2 | 414837 | GTGGAAGCAGGTCACTCAAAC (SEQ ID NO: 21) | CCCCAGTACCAGTTGTTGAATTC (SEQ ID NO: 22) |
| WISP1 | 420322 | AGCCCAACTGCAAATACAACTG (SEQ ID NO: 23) | TGAGTTTGTGCACATGGGAATG (SEQ ID NO: 24) |

Example 3

Permissivity of ESCDL-1 Cells for Replication of Avian Viruses

The Studied Viruses are the Following:
1. Attenuated viruses adapted to cell culture:
   The Bac20 virus and derivatives: the virus Bac20 UL17mRFP (Chbab et al., 2009) was used as a main tool for studying permissivity, because of the facility of its handling (red fluorescent protein fused to the protein UL17) and of the preservation of its multiplication characteristics relatively to the parent virus (non-labeled Bac20). Bacmids coding for the Bac20 and Bac20EGFPUL49 viruses (Blondeau et al., 2008) were also transfected in ESCDL-1 cells. The infection with the infected cells (chicken skin primary cells) with the virus Bac20-eGFPUL49 was also used (Denesvre et al., 2007)
   The virus MeHV-1: The MeHV-1 virus strain FC126 was inoculated on ESCDL-1 cells from a freeze-dried vaccinal preparation (no primary cells).
2. Pathogenic viruses: viruses derived from Bacmids RB-1 B.
   Virus RB-1B and RB-1BUL17mRFP: transfection of bacmids in the ESCDL-1 cells
   RB-1B UL47GFP virus: transmission of the viral infection from transformed T cells (NWB or 3867K) isolated from animals infected with the virus, as described by Jarosinsky et coll. (Jarosinski et al., 2012)

Example 3A

Bac 20 UL17mRFP

The tests were conducted in a first phase with viruses adapted to cell culture, derived from the bacmid coding for the genome of the Bac20 virus. Transfection of a bacmid in ESCDL-1 cells provides a model of study different from the one of the primary cells.

Passage Series and Comparative Titrations on Primary Cells and ESCDL-1 Cells:

TABLE 3

| Passage | Split ratio* | Incubation period | Number of frozen tubes | Titer (PFU/ml) CESkC† | Titer (PFU/ml) ESCDL-1 |
|---|---|---|---|---|---|
| T1** | 5.4 μg Bacmid/4.5 $10^6$ cells | 7 days | | | 250 PFU° |
| P1 | 1/6 | 5 | 3 | ND | ND |
| P2 | 1/5 | 4 | 4 | $(2.6 \pm 0.79) * 10^5$ | $(2.12 \pm 0.71) \times 10^5$ |
| P3 | 1/20 | 6 | 3 | $(3.4 \pm 0.79) * 10^5$ | $(3.05 \pm 0.79) \times 10^5$ |
| P4* | 1/20 | 6 | 3 | | $(1.09 \pm 0.4) \times 10^5$ |
| P5 | 1/10 | 5 | 6 | | $(1.16 \pm 0.09) \times 10^6$ |
| P6 | 1/30 | 5 | 6 | $(5.5 \pm 0.8) * 10^4$ | $(5.2 \pm 0.8) \times 10^4$ |

†CESkC: chicken embryo skin primary cells
P4*: passage on which the viral load was measured in both production systems (CESkC or ESCDL-1)

The replication of the Bac20 UL17mRFP virus in ESCDL-1 results in obtaining infectious titers of the order of 1 to $5 \times 10^5$ PFU/ml as soon as the second passage of the virus in this cell system.

The viral load (number of viral genome copies/cell) measured at passage 4 was equivalent in both production systems (3 to $8 \times 10^3$ viral genome copies per cell for the CESkC cells and 2.4 to $10 \times 10^3$ for ESCDL-1 cells)

Bac20 UL17mRFP: Viral Progeny of Equivalent Titer on CEPP and on ESCDL-1 Under Different Conditions of the Culture Medium of the Cells The results are shown in FIG. 5: The ESCDL-1 have a capability of replicating the virus, equivalent to that of the primary cells (CES kC).

Bac20 UL17mRFP: Equivalent Viral Dissemination on CESkC and on ESCDL-1

Figure 7:
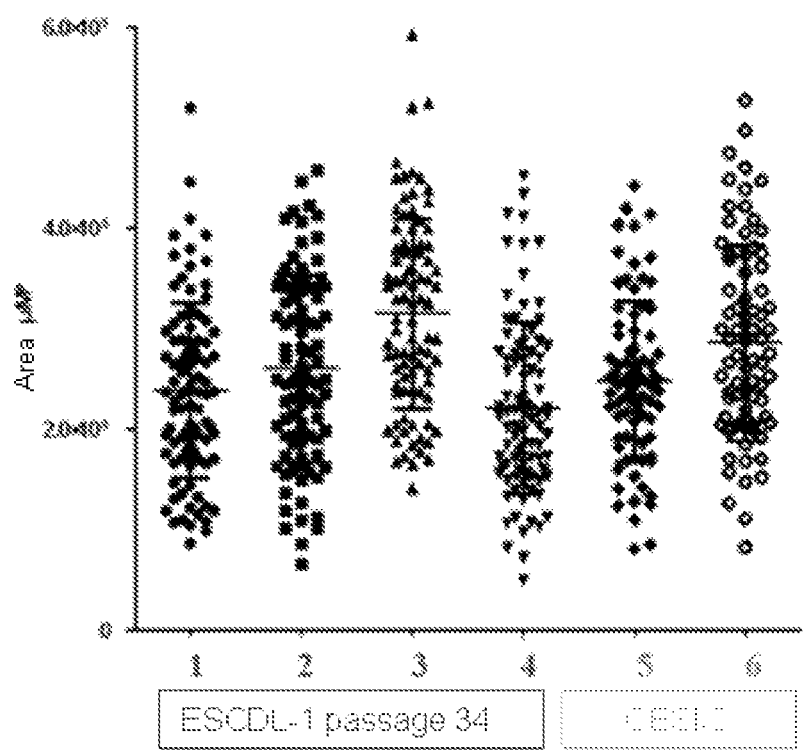
FIG. 7. Viral dissemination—analysis of the size of the ranges induced by the multiplication of the virus on primary cells (CESkC) and on cells of the ESCDL-1 line.

The results are shown in FIG. 7. The analysis of the size of the plates induced by the multiplication of the virus on CESkC or on ESCDL-1 shows a distribution and equivalent size for a same inoculum in both cell systems, regardless of the tested medium conditions.

Example 3B

Bac20 EGFP-UL49 and Bac20

The transfection of Bacmids in ESCDL-1 cells gives the possibility of re-isolating replicative viruses and is expressed by the occurrence of a cytopathogenic effect (plates of infected cells) as soon as the $4^{th}$ day after transfection.

The Bac20 virus obtained from the transfection of the bacmid is replicated in ESCDL-1 cells and the main steps of viral morphogenesis remain similar to those described in CESkC.

As shown in the table below, the ESCDL-1 cells infected with the Bac20 virus show intranuclear capsids of the A, B and C type, intracytoplasmic capsids C and encased capsids between the internal and external nuclear membranes.

TABLE 4

Analysis of the distribution of the capsids in the infected cells:

| Intranuclear A + B + C capsids | Perinuclear capsids | Intra-cytoplasm non-encased capsids | Intra-cytoplasm capsids with teguments | Intra-cytoplasm encased capsids | Total |
|---|---|---|---|---|---|
| 656 | 54 | 356 | 14 | 4 | 1084 |
| 60.52% | 4.98% | 32.84% | 1.29% | 0.37% | 100% |

The count of 1084 capsids in 20 ESCDL-1 cells however gives the possibility of detecting a slightly different distribution from that described for CESkCs, no doubt relating to the difference in the design of the experiment. It is however remarkable to notice that the percentages of intracytoplasm encased capsids (mature capsids) are identical in both cell models (Denesvre et al., 2007).

Example 3C

BacRB-1B

Within the scope of development of a permissive line for replication of *Mardiviruses*, it was important to check that this line allowed replication of fully pathogenic viruses, derived from BacRB-1B (Petherbridge et al., 2004). The transfection of bacmid coding for the RB-1B virus labeled with mRFP on the UL17 protein is expressed by the occurrence of a cytopathogenic viral effect (ECP) as soon as the $4^{th}$ day after transfection. After 3 consecutive passages in ESCDL-1, this virus was titrated on CESkC and on ESCDL-1; the calculated titers are similar (2.5 to $3.5 \times 10^5$ PFU/ml) and on average currently observed for this type of virus produced on primary cells ("standard" cell substrate). We also tested the possibilities of transmitting the viral infection from lymphoid cells NWB and 3867K. Co-cultivation of transformed cells reactivating the virus RB-1B UL47GFP with the ESCDL-1 cells result in the infection of the cells and in the passage of the virus into a lytic cycle in the ESCDL-1 cells.

Example 3D

The MeHV1 Virus:

The virus was inoculated on ESCDL-1 cells under the indicated conditions and this inoculation is expressed by the occurrence of a cytopathogenic effect. The virus resulting from this first passage was titrated on CESkC and ESCDL-1. The viral titers, measured in PFU, are identical ($4.05 \pm 0.9 \times 10^4$).

Example 3E

The Birnavirus

The IBDV virus of the strain CT (strain CT, access number GENBANK EMBL AJ310185) adapted to the cell culture was produced either in CEPP or in ESCDL-1 and the titrated viral progeny in a limiting dilution in both cell systems. The obtained titers are $1 \times 10^{6.79}$ TCID50 on CESkC and of $1 \times 10^{6.77}$ TCID50 on ESCDL-1.

The result of the titration of the IBDV viruses produced on the primary cells (IBDV-PP1H+ or H−) or on ESCDL-1 cells (IBDV-ESCDL-1 34 or 69H+ or H−) on secondary cells (PP2) or on ESCDL-1 cells at passage 39 is shown in table 5 below:

| IBDV virus produced on | Cells used for the titration | |
|---|---|---|
| | CESkC (P2)† | ESCDL-1 P39 |
| CESkC | $1 \times 10^{6.79}$ | $1 \times 10^{7.03}$ |
| ESCDL-1 P34 | $1 \times 10^{6.77}$ | $1 \times 10^{6.77}$ |
| ESCDL-1 P69 | $1 \times 10^{6.65}$ | $1 \times 10^{6.53}$ |

†CESkC P2: secondary cells obtained by trypsination and putting the CESkC back into culture.

This table gives an idea of the stability of the phenotype of ESCDL-1 cells which prove to be as sensitive to infection by IBDV at passages 34 or 69. The viral titers (calculated according to the Reed and Muench method) are similar among the CESkC and the ESCDL-1 cells.

Example 4

Transfection of the ESCDL-1 Line

Example 4A

ESCDL-1 Venus: a Line Expressing an EYFP

The ESCDL-1 cells at passage 21 were co-transfected with the pCS2Venus plasmid and the pTK-Hyg2 plasmid (resistance to hygromycin) in a molar ratio of 20 molecules of pCS2Venus/1 molecule of pTK-Hyg2. After transfection (Nucleofector Amaxa—Basic Fibroblast kit—program F024), the cells were selected with hygromycin (80 µg/ml). The ESCDL-1_Venus obtained after cloning strong express the fluorescent protein, which is localized in the cytoplasm and the nucleus, and replicate the *Mardiviruses*.

The ESCDL-1_Venus cells may thus be used as a substrate for studying the transmission conditions of the viral infection (cell-to-cell transmission).

Example 4B

ESCDL-1 UL37: Transcomplementing Line for an Essential Viral Gene.

We produced several bacmids coding for viruses including mutations invalidating an essential gene, UL37, coding for a tegument protein. The mutations relate to the whole of the gene (deletion) or to 2 codons coding for 2 participating leucines of a <<pseudo leucine zipper>> unit, a unit preserved in many UL37 orthologs (a gene preserved in all herpes viruses). ESCDL-1 lines transfected with a pCDNA3-UL37 (ESCDL-1_37) or pCDNA3-UL37-mut (ESCDL-1_37mut) were selected and tested for their capability of replicating mutant and parent viruses from transfected bacmids. We were able to observe the formation of plates and the genesis of a viral progeny for both mutated viruses (deletion and one-off mutation) on the sole ESCDL-1_37 cells. Neither ESCDL-1 nor ESCDL-1_37mut expressing the mutated protein are able to complement the mutant viruses.

In the present scientific context, the ESCDL-1 line appears to be the only <<usable>> line for this kind of study, the QM7 cells described earlier (Schumacher et al., 2002) do not have equivalent permissivity for the whole of the Mardiviruses.

Example 4C

ESCDL-1 Lc3-GFP and LBR-GFP: Cell Clones Expressing Cell Proteins Fused to EGFP (Enhanced Green Fluorescent Protein)

Different ESCDL-1 cell clones expressing the Lc3-EGFP proteins (marker of autophagy) and the LBR-EGFP proteins (receptor of lamin B) were generated. By stable expression of the transgene, these lines give the possibility of studying the cell response (autophagy and destabilization of the nuclear lamina) during pathological processes in particular during infections with DNA and RNA viruses (for example, avian influenza viruses capable of activating autophagic processes). The major benefit of these stable lines is to follow in real time the relocalization of the Lc3 and LBR proteins in the cell during infection.

The ESCDL-1 lines expressing a recombinase, Flippase, were also obtained; the expression of the transgene was established and the Flippase activity is being characterized.

Because of the ease and rapidity of establishing ESCDL-1 lines expressing labeled cell proteins (about 1 month), the extension of this system to a wider panel of proteins may be contemplated.

REFERENCES

Patents

WO 2007/110343
WO 98/006824
EP 2 572 728
EP 0 775 743

Non-Patents

Blondeau, Marc, Courvoisier, Vautherot & Denesvre (2008). *Functional homologies between avian and human alpha-herpesvirus VP22 proteins in cell-to-cell spreading as revealed by a new cis-complementation assay*. J Virol 82, 9278-9282.

Chbab, Chabanne-Vautherot, Francineau, Osterrieder, Denesvre & Vautherot (2009). *The Marek's disease virus (MDV) protein encoded by the UL17 ortholog is essential for virus growth*. Vet Res 40, 28.

Churchill (1968). *herpes-type virus isolated in cell culture from tumours of chickens with Marek's disease. I. Studies in cell culture*. J Natl Cancer Inst 41, 939-950.

Coraux, Hilmi, Rouleau, Spadafora, Hinnrasky, Ortonne, Dani & Aberdam (2003). *Reconstituted skin from murine embryonic stem cells*. Curr Biol 13, 849-853.

Correia, Anisimov, Li & Brundin (2008). *Growth Factors and Feeder Cells Promote Differentiation of Human Embryonic Stem Cells into Dopaminergic Neurons: A Novel Role for Fibroblast Growth Factor-20*. Front Neurosci, 2, 26-34.

Denesvre, Blondeau, Lemesle, Le Vern, Vautherot, Roingeard & Vautherot (2007). *Morphogenesis of a highly replicative EGFPVP22 recombinant Marek's disease virus in cell culture*. J Virol 81, 12348-12359.

Dorange, El Mehdaoui, Pichon, Coursaget & Vautherot (2000). *Marek's disease virus (MDV) homologues of herpes simplex virus type 1 UL49 (VP22) and UL48 (VP16) genes: high-level expression and characterization of MDV-1 VP22 and VP16*. J Gen Virol 81, 2219-2230.

Esnault, Bonsergent, Larcher, Bed'hom, Vautherot, Delaleu, Guigand, Soubieux, Marc & Quéré (2011). *A novel chicken lung epithelial cell line: Characterization and response to low pathogenicity avian influenza virus*. Virus Res 159, 32-42.

Eyal-Giladi & Kovak (1976). *From cleavage to primitive streak formation: a complementary normal table and a new look at the first stages of the development of the chick; I. General Morphology*. Dev. Biol 49, 321-337.

Fuchs & Mettenleiter (1999). *DNA sequence of the UL6 to UL20 genes of infectious laryngotracheitis virus and characterization of the UL10 gene product as a nonglycosylated and nonessential virion protein*. J Gen Virol 80 (Pt 8), 2173-2182.

Geerligs, Quanz, Suurland, Spijkers, Rodenberg, Davelaar, Jongsma, Kumar (2008). *Efficacy and safety of cell associated vaccines against Marek's disease virus grown in a continuous cell line from chickens*. Vaccine. 26, 5595-5600.

Jarosinski, Arndt, Kaufer & Osterrieder (2012). *Fluorescently tagged pUL47 of Marek's disease virus reveals differential tissue expression of the tegument protein in vivo*. J Virol 86, 2428-2436.

Jarosinski, Margulis, Kamil, Spatz, Nair & Osterrieder (2007). *Horizontal transmission of Marek's disease virus requires US2, the UL13 protein kinase, and gC*. J Virol 81, 10575-10587.

Jarosinski, Yunis, O'Connell, Markowski-Grimsrud & Schat (2002). *Influence of genetic resistance of the chicken and virulence of Marek's disease virus (MDV) on nitric oxide responses after MDV infection*. Avian Dis 46, 636-649.

Kawaguchi, Nomura, Hirayama & Kitagawa (1987). *Establishment and characterization of a chicken hepatocellular carcinoma cell line, LMH*. Cancer Res, 47, 4460-4463.

Kawasaki, Mizuseki, Nishikawa, Kaneko, Kuwana, Nakanishi, Nishikawa & Sasai (2000). *Induction of midbrain dopaminergic neurons from ES cells by stromal cell-derived inducing activity*. Neuron 28, 31-40.

Lavial, Acloque, Bertocchini, Macleod, Boast, Bachelard, Montillet, Thenot, Sang, Stern, Samarut & Pain (2007). *The Oct4 homologue PouV and Nanog regulate pluripotency in chicken embryonic stem cells*. Development, 134, 3549-3563.

Lee, Foster, Bottje, Jang, Chandra, Gentles & Kong. (2013). *Establishment of an immortal chicken embryo liver-derived cell line*. Poult Sci. 92,1604-1612

Lejal, Da Costa, Huet & Delmas (2000). *Role of Ser-652 and Lys-692 in the protease activity of infectious bursal disease virus VP4 and identification of its substrate cleavage sites*. J Gen Virol 81, 983-992.

Marks & Rifkind (1989). *Induced differentiation of erythroleukemia cells by hexamethylene bisacetamide: a model for cytodifferentiation of transformed cells*. Environ Health Perspect. 80, 181-188.

Moscovici, Moscovici, Jimenez, Lai, Hayman & Vog (1977). *Continuous tissue culture cell lines derived from chemically induced tumors of Japanese quail*. Cell. 11, 95-103.

Mou, Pitel, Gourichon, Vignoles, Tzika, Tato, Yu, Burt, Bed'hom, Tixier-Boichard, Painter & Headon (2011). *Cryptic patterning of avian skin confers a developmental facility for loss of neck feathering*. PLoS Biol 9, e1001028.

Nakano, Kodama & Honjo (1994). *Generation of lymphohematopoietic cells from embryonic stem cells in culture*. Science 265, 1098-1101.

Ogura & Fujiwara. (1987). *Establishment and characterization of a virus-free chick cell line. Acta Med Okayama*. 41,141-143.

Pain, Clark, Shen, Nakazawa, Sakurai, Samarut & Etches (1996). *Long-term in vitro culture and characterisation of avian embryonic stem cells with multiple morphogenetic potentialities*. Development 122, 2339-2348.

Panacchia, Dellambra, Bondanza, Paterna, Maurelli, Paionni & Guerra. (2010). *Nonirradiated human fibroblasts and irradiated 3T3-J2 murine fibroblasts as a feeder layer for keratinocyte growth and differentiation in vitro on a fibrin substrate*. Cells Tissues Organs 191, 21-35.

Petherbridge, Brown, Baigent, Howes, Sacco, Osterrieder & Nair (2004). *Oncogenicity of virulent Marek's disease virus cloned as bacterial artificial chromosomes*. J Virol 78, 13376-13380.

Preston & McFarlane (1998). *Cytodifferentiating agents affect the replication of herpes simplex virus type 1 in the absence of functional VP16*. Virology 249, 418-426.

Richerioux, Blondeau, Wiedemann, Remy, Vautherot & Denesvre (2012). *Rho-ROCK and Rac-PAK Signaling Pathways Have Opposing Effects on the Cell-to-Cell Spread of Marek's Disease Virus*. PLoS One 7, e44072.

Schumacher, Tischer, Fuchs & Osterrieder (2000). *Reconstitution of Marek's disease virus serotype 1 (MDV-1) from DNA cloned as a bacterial artificial chromosome and characterization of a glycoprotein B-negative MDV-1 mutant*. J Virol 74, 11088-11098.

Schumacher, Tischer, Teifke, Wink & Osterrieder (2002). *Generation of a permanent cell line that supports efficient growth of Marek's disease virus (MDV) by constitutive expression of MDV glycoprotein E*. J Gen Virol 83, 1987-1992.

Solomon, Witter, Nazerian, Burmester (1968). *Studies on the Etiology of Marek's Disease. I. Propagation of the Agent in Cell Culture*. Exp Biol Med 127, 173-177

Storlie, Jackson, Hutchinson & Grose (2006). *Delayed biosynthesis of varicella-zoster virus glycoprotein C: upregulation by hexamethylene bisacetamide and retinoic acid treatment of infected cells*. J Virol 80, 9544-9556.

The invention claimed is:

1. A vaccinal preparation comprising a non-transformed avian cell line allowing replication of avian viruses in vitro; wherein the non-transformed avian cell line is made by a method comprising:
   a) cultivating avian embryonic stem cells in the presence of a stroma for at least 3 days;
   b) cultivating in a medium with a low serum concentration for at least 2 days;
   c) cultivating in a low serum concentration medium comprising between 1 and 10 mM of hexamethylene bisacetamide (HMBA), for at least 2 days; and
   d) cultivating in a low serum concentration medium for at least 10 days;

to thereby provide a non-transformed avian cell line allowing replication of avian viruses, wherein the non-transformed avian cell line expresses the following markers: CD44+, beta1 integrin, collagen 1 and OLFM3; and wherein the non-transformed avian cell line is infected with at least one avian virus.

* * * * *

SEQUENCE LISTING

```
<160> NUMBER OF SEQ ID NOS: 24

<210> SEQ ID NO 1
<211> LENGTH: 22
<212> TYPE: DNA
<213> ORGANISM: artificial
<220> FEATURE:
<223> OTHER INFORMATION: Forward primer of AP1S3 gene

<400> SEQUENCE: 1
tgcggtgaaa gccatggaag ac                                          22

<210> SEQ ID NO 2
<211> LENGTH: 27
<212> TYPE: DNA
<213> ORGANISM: artificial
<220> FEATURE:
<223> OTHER INFORMATION: Reverse primer of AP1S3 gene

<400> SEQUENCE: 2
gcaggtgtgt acagcagttc tctttcc                                     27

<210> SEQ ID NO 3
<211> LENGTH: 22
<212> TYPE: DNA
<213> ORGANISM: artificial
<220> FEATURE:
<223> OTHER INFORMATION: Forward primer of cPOUV/OCT4 gene
```

```
<400> SEQUENCE: 3
tgcaatgcag agcaagtgct gg                                          22

<210> SEQ ID NO 4
<211> LENGTH: 22
<212> TYPE: DNA
<213> ORGANISM: artificial
<220> FEATURE:
<223> OTHER INFORMATION: Reverse primer of cPOUV/OCT4 gene

<400> SEQUENCE: 4
actgggcttc acacatttgc gg                                          22

<210> SEQ ID NO 5
<211> LENGTH: 27
<212> TYPE: DNA
<213> ORGANISM: artificial
<220> FEATURE:
<223> OTHER INFORMATION: Forward primer of ECM2 gene

<400> SEQUENCE: 5
gtcagaaatt tgctttaacc acacaag                                     27

<210> SEQ ID NO 6
<211> LENGTH: 25
<212> TYPE: DNA
<213> ORGANISM: artificial
<220> FEATURE:
<223> OTHER INFORMATION: Reverse primer of ECM2 gene

<400> SEQUENCE: 6
tttatccaag ccaaaggtgc tattc                                       25

<210> SEQ ID NO 7
<211> LENGTH: 20
<212> TYPE: DNA
<213> ORGANISM: artificial
<220> FEATURE:
<223> OTHER INFORMATION: Forward primer of EDN2 gene

<400> SEQUENCE: 7
ctggagccca aggcagacgc                                             20

<210> SEQ ID NO 8
<211> LENGTH: 20
<212> TYPE: DNA
<213> ORGANISM: artificial
<220> FEATURE:
<223> OTHER INFORMATION: Reverse primer of EDN2 gene

<400> SEQUENCE: 8
ggccagtgat gcgggcactt                                             20

<210> SEQ ID NO 9
<211> LENGTH: 23
<212> TYPE: DNA
<213> ORGANISM: artificial
<220> FEATURE:
<223> OTHER INFORMATION: Forward primer of HELLS gene

<400> SEQUENCE: 9
aagctctgct ggcaacctgt gtc                                         23

<210> SEQ ID NO 10
<211> LENGTH: 23
```

```
<212> TYPE: DNA
<213> ORGANISM: artificial
<220> FEATURE:
<223> OTHER INFORMATION: Reverse primer of HELLS gene

<400> SEQUENCE: 10
aggaactgct tggcactgtg tcg                                          23

<210> SEQ ID NO 11
<211> LENGTH: 20
<212> TYPE: DNA
<213> ORGANISM: artificial
<220> FEATURE:
<223> OTHER INFORMATION: Forward primer of KRT19 gene

<400> SEQUENCE: 11
ggcttcggtg gtggctatgg                                              20

<210> SEQ ID NO 12
<211> LENGTH: 20
<212> TYPE: DNA
<213> ORGANISM: artificial
<220> FEATURE:
<223> OTHER INFORMATION: Reverse primer of KRT19 gene

<400> SEQUENCE: 12
aggacgcgag gcggtcattc                                              20

<210> SEQ ID NO 13
<211> LENGTH: 20
<212> TYPE: DNA
<213> ORGANISM: artificial
<220> FEATURE:
<223> OTHER INFORMATION: Forward primer of KRT8 gene

<400> SEQUENCE: 13
ccggcagctg cgtgagtacc                                              20

<210> SEQ ID NO 14
<211> LENGTH: 20
<212> TYPE: DNA
<213> ORGANISM: artificial
<220> FEATURE:
<223> OTHER INFORMATION: Reverse primer of KRT8 gene

<400> SEQUENCE: 14
cgtggtccgg gtgtggatgc                                              20

<210> SEQ ID NO 15
<211> LENGTH: 23
<212> TYPE: DNA
<213> ORGANISM: artificial
<220> FEATURE:
<223> OTHER INFORMATION: Forward primer of  NANOG gene

<400> SEQUENCE: 15
tgcacaccag gcttacagca gtg                                          23

<210> SEQ ID NO 16
<211> LENGTH: 22
<212> TYPE: DNA
<213> ORGANISM: artificial
<220> FEATURE:
<223> OTHER INFORMATION: Reverse primer of  NANOG gene

<400> SEQUENCE: 16
```

```
tgctgggtgt tgcagcttgt tc                                        22

<210> SEQ ID NO 17
<211> LENGTH: 21
<212> TYPE: DNA
<213> ORGANISM: artificial
<220> FEATURE:
<223> OTHER INFORMATION: Forward primer of OLFM3 gene

<400> SEQUENCE: 17
tgggcaggaa ccaaccacgt t                                         21

<210> SEQ ID NO 18
<211> LENGTH: 20
<212> TYPE: DNA
<213> ORGANISM: artificial
<220> FEATURE:
<223> OTHER INFORMATION: Reverse primer of OLFM3 gene

<400> SEQUENCE: 18
gtgcaagcac ccgcccagta                                           20

<210> SEQ ID NO 19
<211> LENGTH: 20
<212> TYPE: DNA
<213> ORGANISM: artificial
<220> FEATURE:
<223> OTHER INFORMATION: Forward primer of RSP17 gene

<400> SEQUENCE: 19
acacccgtct gggcaacgac                                           20

<210> SEQ ID NO 20
<211> LENGTH: 20
<212> TYPE: DNA
<213> ORGANISM: artificial
<220> FEATURE:
<223> OTHER INFORMATION: Reverse primer of RSP17 gene

<400> SEQUENCE: 20
cccgctggat gcgcttcatc                                           20

<210> SEQ ID NO 21
<211> LENGTH: 21
<212> TYPE: DNA
<213> ORGANISM: artificial
<220> FEATURE:
<223> OTHER INFORMATION: Forward primer of THBS2 gene

<400> SEQUENCE: 21
gtggaagcag gtcactcaaa c                                         21

<210> SEQ ID NO 22
<211> LENGTH: 23
<212> TYPE: DNA
<213> ORGANISM: artificial
<220> FEATURE:
<223> OTHER INFORMATION: Reverse primer of THBS2 gene

<400> SEQUENCE: 22
ccccagtacc agttgttgaa ttc                                       23

<210> SEQ ID NO 23
<211> LENGTH: 22
<212> TYPE: DNA
<213> ORGANISM: artificial
```

```
<220> FEATURE:
<223> OTHER INFORMATION: Forward primer of WISP1 gene

<400> SEQUENCE: 23
agcccaactg caaatacaac tg                                              22

<210> SEQ ID NO 24
<211> LENGTH: 22
<212> TYPE: DNA
<213> ORGANISM: artificial
<220> FEATURE:
<223> OTHER INFORMATION: Reverse primer of WISP1 gene

<400> SEQUENCE: 24
tgagtttgtg cacatgggaa tg                                              22
```